(12) United States Patent
Epshtein et al.

(10) Patent No.: US 7,700,096 B2
(45) Date of Patent: Apr. 20, 2010

US007700096B2

(54) MEDICINAL AGENT FOR TREATING ERECTILE DYSFUNCTION

(75) Inventors: Oleg Iliich Epshtein, B.Kazeni per., d. Y kv 41, Moscow 103064 (RU); Evgeny Danilovich Goldberg, Tomsk (RU); Alexandr Mikhailovich Dygay, Tomsk (RU)

(73) Assignee: Oleg Iliich Epshtein, Moscow (RU)

( * ) Notice: Subject to any disclaimer, the term of this patent is extended or adjusted under 35 U.S.C. 154(b) by 656 days.

(21) Appl. No.: 10/522,650

(22) PCT Filed: Aug. 2, 2002

(86) PCT No.: PCT/RU02/00368

§ 371 (c)(1),
(2), (4) Date: Jan. 22, 2005

(87) PCT Pub. No.: WO2004/012767

PCT Pub. Date: Feb. 12, 2004

(65) Prior Publication Data

US 2006/0165697 A1 Jul. 27, 2006

(51) Int. Cl.
*A61K 39/395* (2006.01)

(52) U.S. Cl. .................................. 424/130.1

(58) Field of Classification Search ............ None
See application file for complete search history.

(56) References Cited

U.S. PATENT DOCUMENTS

| | | | |
|---|---|---|---|
| 3,032,584 A | 5/1962 | Stock et al. | |
| 3,134,718 A | 5/1964 | Nobile | |
| 3,901,967 A | 8/1975 | Cohen et al. | |
| 4,292,324 A | 9/1981 | Jonsson et al. | |
| 4,839,341 A | 6/1989 | Massey et al. | |
| 4,963,367 A | 10/1990 | Ecanow | |
| 4,987,127 A | 1/1991 | Sirany | |
| 5,629,286 A | 5/1997 | Brewitt | |
| 5,683,712 A | 11/1997 | Cavazza | |
| 5,698,195 A | 12/1997 | Le et al. | |
| 5,741,488 A * | 4/1998 | Feldman et al. | 424/154.1 |
| 5,846,514 A | 12/1998 | Foster et al. | |
| 5,879,677 A | 3/1999 | del Zoppo | |
| 6,136,309 A | 10/2000 | Novick et al. | |
| 6,143,722 A | 11/2000 | Melin et al. | |
| 6,150,500 A * | 11/2000 | Salerno | 530/300 |
| 6,326,360 B1 | 12/2001 | Kanazawa et al. | |
| 6,750,197 B1 | 6/2004 | Salerno | |
| 2003/0099636 A1 | 5/2003 | Epshtein et al. | |
| 2005/0266007 A1 | 12/2005 | Epshtein et al. | |
| 2006/0024307 A1 | 2/2006 | Epshteni et al. | |
| 2006/0165697 A1 | 7/2006 | Epshtein et al. | |
| 2007/0123518 A1 | 5/2007 | Epshtein et al. | |
| 2008/0025985 A1 | 1/2008 | Iliich et al. | |

FOREIGN PATENT DOCUMENTS

| | | |
|---|---|---|
| DE | WO/99/21582 A2 | 10/1998 |
| EP | 0687466 A1 | 12/1995 |
| RU | 0884042 A1 | 8/1997 |
| RU | WO/98/14161 A1 | 4/1998 |
| RU | WO/98/14162 A1 | 4/1998 |
| RU | WO/98/14166 A1 | 4/1998 |
| RU | WO/98/33493 A1 | 8/1998 |
| RU | WO/98/35680 A1 | 8/1998 |
| RU | 96113138 A | 10/1998 |
| RU | WO/01/05371 A1 | 1/2001 |
| SU | 1331508 A1 | 8/1987 |
| SU | 1730144 A1 | 4/1992 |
| SU | 1836083 A3 | 8/1993 |
| WO | WO/03/037372 A1 | 5/2003 |
| WO | WO/03/055518 A1 | 7/2003 |
| WO | WO/03/055519 A1 | 7/2003 |
| WO | WO/03/077946 A1 | 9/2003 |
| WO | WO/2004/012765 A1 | 2/2004 |

OTHER PUBLICATIONS

Davenas et al., Nature, 1988, 333:816-818.*
Epshtein et al., Bulletin of experimental Biology and Medicine, 1999, 5:493-495.*
Janeway et al., Immunobiology, 1997, 3rd edition, Garland Publishing Inc., pp. 3:1-3:11.*
International Search Report from International Application No. PCT/RU02/00368, filed Aug. 2, 2002, mailed on Dec. 5, 2002.
Marsden, P. A. et al., "Molecular cloning and characterization of human endothelial nitric oxide synthase," FEBS Lett., vol. 307, No. 3, pp. 287-293, 1992.
Register of Pharmaceuticals in Russia, Encyclopedia of Pharmaceuticals (in Russian), Moscow, 2001, pp. 788-789.
Schwabe, W., "German Homoeopathic Pharmacopoeia (Homoeopathisches Arzneibuch)," Stuttgart, Translation of the 5th Supplement (1991) to the 1978 edition.
Vyazov, O. L., Laboratory Methods of Studies in Non-Infection Immunology (in Russian), Moscow, Meditsina, 1968.

(Continued)

*Primary Examiner*—Ilia Ouspenski
(74) *Attorney, Agent, or Firm*—Kaplan Gilman & Pergament LLP

(57) ABSTRACT

A medicament based on antibodies contains an activated form of ultra-low doses of monoclonal, polyclonal, or natural antibodies to endothelial nitric oxide synthase (NO synthase), the activated form being prepared by multiple consecutive dilutions and exposure to external factors, preferably according to the homeopathic technology. A method of treating erectile dysfunctions and vegetative disturbances of male climax by regulating the level of cyclic guanosine monophosphate (cGMP) in the cavernous bodies on sexual stimulation, the method being characterized by the use of activated forms of ultra-low doses of antibodies to the entire molecule of the endothelial NO synthase or to its polypeptide fragments, activated forms being prepared by multiple consecutive dilutions and exposure to external factors.

8 Claims, No Drawings

OTHER PUBLICATIONS

Borovskaya, et al., Impact Of Antibodies To Endothelial No-Synthase On Sexual Behavior Of Male Rats In Conditions Of Seasonal Suppression Of Reproductive Function, Scientific-Research Institute of pharmacology (2001) (Translation).

International Search Report from International Application No. PCT/RU01/00239, filed Jun. 19, 2001, mailed on Sep. 20, 2001.

International Search Report from International Application No. PCT/RU02/00367, filed Aug. 2, 2002, mailed on Dec. 19, 2002.

International Search Report from International Application No. PCT/RU02/00369, filed Aug. 2, 2002, mailed on Dec. 26, 2002.

International Search Report from International Application No. PCT/RU02/00365, filed Aug. 2, 2002, mailed on Dec. 5, 2002.

International Search Report from International Application No. PCT/RU2006/000237, filed May 16, 2006, mailed on Nov. 23, 2006.

Beregovoy et al., On Influence of Various Dilutions of Monoclonal Antibodies 5F5-B6 on the Formation of Long-Term Post-Tetanic Potentiation in Survived Hippocampal Slices, Bull of Siberian Branch of RAMS No. 1 (91), 1999.

Pavlov et al., "Behavioral Effects of Potentiated Morphine Forms," Bull of Siberian Branch of RAMS No. 1 (91), 1999.

Zapara et al., "Potentiated Morphine Effect On The Electric Properties Of Isolated Neurons." Bull of Siberian Branch of RAMS, No. 1 (91), (1999).

Frimel, G., ed., "immunological methods, "Medicina publishing House, 1987, pp. 9-33.

Skurkovich, et al. Multiple Sclerosis Randomized study of antibodies to IFN-γ and TNF-α in secondary progressive multiple sclerosis, 7:277-284, (2001).

Alexandrova et al., "An Experience of Application of Potentiated Compounds for Jugulation of Alcohol Abstinent Syndrome and Opiate Abstinent Syndrome," Bull of Siberian Branch of RAMS, No. 1 (91), 1999.

Maini, R. N. et al., "Anti-Cytokine Therapy for Rheumatoid Arthritis," Annu. Rev. Med. 51:207-229 (2000).

White et al., "Radioimmunotherapy of relapsed B-cell lymphoma with yttrium 90 anti-idiotype monoclonal antibodies," Blood, vol. 87: 3640-3649 (1996).

Linde et al., "Are the clinical effects of homeopathy placebo effects? A meta-analysis of placebo-controlled trials," Lancet, vol. 350: 836-43 (1997).

* cited by examiner

MEDICINAL AGENT FOR TREATING ERECTILE DYSFUNCTION

FIELD OF THE INVENTION

The preset invention relates to the field of medicine and can be used for treating the disturbances in erection of various origin and vegetative impairments during male climax.

BACKGROUND OF THE INVENTION

It is a well-known practice of the treatment of pathologic syndromes by the use of antibodies (SU 1331508 A, A 61 K 39/00, 1984; SU 1730144 A1, C 12 N 7/00, 1992).

The disturbances in erection can be treated by regulation of the levels of cyclic guanosine monophosphate (cGMP) in the cavernous bodies on sexual stimulation (see Register of Pharmaceuticals in Russia, Encyclopedia of Pharmaceuticals (in Russian), Moscow, 2001, pp. 788-789). This approach enhances the relaxing effect of nitric oxide (NO) on the smooth muscles of the cavernous bodies and increases penile blood flow through the administration of a direct inhibitor of cGMP-specific phosphodiesterase Type 5. However, the duration of this effect is limited to 3-5 hours and the agent used (sildenafil citrate) is contraindicated to persons receiving nitric oxide donors or nitrates in any form.

DESCRIPTION OF THE INVENTION

The present invention is directed at obtaining an efficient medication for and a method of the treatment of erectile dysfunctions of various origin and of vegetative disorders of male climax.

The formulated objective is attained by using a medication containing an activated form of ultra-low doses of monoclonal, polyclonal or natural antibodies to endothelial nitric oxide synthase (NO synthase), the activated form being prepared by multiple consecutive dilutions and by exposure to external factors, preferably in accordance with homeopathic technology.

For preparing the antibodies one can use the entire molecule or polypeptide fragments of the enzyme (endothelial NO synthase).

The method of the treating erectile dysfunctions of various origin and of vegetative disorders of male climax through regulation of the level of cyclic guanosine monophosphate (cGMP) in the cavernous bodies on sexual stimulation involves the use of activated forms of ultra-low doses of antibodies to the entire molecule of endothelial NO synthase or to its polypeptide fragments, the activated forms being prepared by multiple consecutive dilutions and exposure to external factors.

Preferably, a mixture of various, mostly centemal, homeopathic dilutions of the antibodies indicated above should be employed.

The medication obtained in accordance with the present invention is a new pharmaceutical, which modifies the activity of NO synthase, thus intensifying the synthesis of nitric oxide in the cavernous bodies on sexual stimulation and enhancing the penile blood flow.

Unlike physiologic (therapeutic) doses of the antibodies, the activated forms of ultra-low doses of the antibodies to NO synthase do not bind (inactivate) the enzyme; instead, they modify its effects. The new medication has an effect synergic with that of NO synthase. The existence of the therapeutic effect of ultra-low doses of antibodies activated by homeopathic technology, as well as the unidirectional character of the action with the original enzyme do not follow from the state-of-the-art knowledge and have been discovered by the inventor.

EMBODIMENTS OF THE INVENTION

The new pharmaceutical is preferably prepared in the following manner.

A synthetic polypeptide corresponding to the fragment of the endothelial (Type III) NO synthase (1185-1205) with the following amino acid sequence: Glu Arg Leu His Asp Ile Glu Ser Lys Gly Leu Gln Pro Thr Pro Met Thr Leu Val Phe is obtained by solid-phase peptide synthesis (Marsden P A, Schappert K T, Chen H S, Flowers M, Sundell C L, Wilcox J N, Lamas S, Michel T Molecular Cloning and Characterization of Human Endothelial Nitric Oxide Synthase, FEBS Lett., 307:287-293, 1992).

The produced peptide, conjugated with methylated bovine serum albumin as a carrier, is used as an immunogen for immunization of rabbits. The monospecific serum to NO synthase is obtained by immunization of rabbits by this immunogen in accordance with a well-known procedure (Vyazov O. L. Laboratory Methods of Studies in Non-Infection Immunology (in Russian), Moscow, Meditsina, 1968, 356 pages). The blood is taken from an external ear vein into sterile test tubes. After the clot retraction, the serum is separated by centrifugation and heated at 56° C. for 10 min for complement inactivation.

The isolated antibodies to the endothelial NO synthase are subjected to consecutive multiple dilutions and exposed to an external mechanical impact until ultra-low or low doses are obtained, for example, according to homeopathic technology of potentization (see W. Schwabe, "Homöopathisches Arzneibuch", Stuttgart, 1978). This procedure gives rise to a uniform decrease in concentration through consecutive dilutions of 1 volumetric part of the initial matter (antibodies) in 9 volumetric parts (for decimal dilution, D) or in 99 volumetric parts (for centimal dilution, C) of a neutral solvent with multiple vertical shaking of each solution; the advantages of various containers for each subsequent dilution are used. Finally, this procedure gives the required dose (potency).

The external treatment in the course of concentration reduction can be also executed by exposure to ultrasonic, electromagnetic, or other physical factors.

The resultant medicines are used mostly in the dosage forms and dilutions adopted in the homeopathic practice: as alcoholic and aqueous solutions or as tablets (granules) prepared by impregnating the carrier contained in the dosage form by the potentised solution to saturation; also, the potentised solution can be added directly to a liquid dosage form.

Example 1

In studies of the effect of activated forms of ultra-low doses of antibodies to the endothelial NO synthase on the sexual behavior of adult male rats being under conditions of physiologic suppression of the reproductive function, we administered per os potentiated antibodies to NO synthase in a mixture of homeopathic dilutions C12+C30+C200 (within a period of 5 days, 1.5 ml per animal) to male rats 16 months old weighing 600-700 g with an established degree of sexual function suppression. After that, the male rats were placed with female rats (4 months old, weight 300 g) being in the estrous stage of the sexual cycle. Within 15 min we were registering the copulative activity on the basis of the following parameters for each male: latency of mounting (the period between the first presentation of the female and the first mounting), the number of courtships (sniffings, lickings), the total number of mountings, the number of copulations.

It was found that after 5 administrations of the preparation the number of courtships increased with high degree of significance (2 times) as against the initial indices of all animals; in 55.5% of the animals (with the initial medium and pronounced sexual activity) the indices of sexual activity increased with high degree of significance. All this testified to the stimulating effect on the sexual activity of male rats present under the conditions of physiologic suppression of the reproductive function.

Example 2

In studies of the effect of activated forms of ultra-low doses of antibodies to endothelial NO synthase on the sexual behavior of adult male rats being under conditions of seasonal suppression of the reproductive function we administered per os potentiated polyclonal antibodies to NO synthase in a mixture of homeopathic dilutions C12+C30+C200 (within a period of 5 days, 1.5 ml per animal) to male rats 4 months old weighing 400-450 g. After that, the male rats were placed with female rats (4 months old, weight 300 g) being in the estrous stage of the sexual cycle. Within 15 min we were registering the copulative activity on the basis of the following parameters for each male: the latency of mounting (the period between the first presentation of the female and the first mounting), the number of courtships (sniffings, lickings), the total number of mountings, the number of copulations.

It was found that after 5 administrations of the preparation the latency of mounting in the test group decreased with high degree of significance; at the same time, we observed an increase in the total number of mountings (2-fold) and in the number of copulations (3-fold) as against the indices obtained for the animals before administration of the drug. Thus, the administration of the preparation gave rise to the improvement of the copulative activity in male rats being under the conditions of seasonal suppression of the reproductive function, the improvement being manifested in the animals' need for repeated coitions. The accompanying decrease in the number of courtships was caused by a higher copulative activity.

Example 3

Patient S. (male), aged 51, applied to the urologist with a complaint about decreased libido, erection impairment, and lowered satisfaction from the coitus. These symptoms had been aggravating during previous two years. Over the recent 3 years the patient had been marking periodic suppressed mood, whining, memory and sleep disorders, lowered working capacity, palpitation fits, instability of the arterial blood pressure. Clinical findings: a moderate enlargement of the prostate gland. Diagnosis: erectile dysfunction against the background of involutional hormonal changes. Prescription: a mixture of homeopathic dilutions C12+C30+C200 of monoclonal antibodies to a fragment of human endothelial NO synthase, 1 tablet every 3 days. Two weeks after the beginning of treatment the patient noted better erection and an enhancement of libido against the background of the improvement of the general condition: the overall tonicity rose and the sleep became better. The recommendation was to take the preparation 1-2 times a week. On the second visit 2 months after the beginning of the treatment the patient presented no complaints; he regained libido, erection, and satisfaction from the coitus.

The invention claimed is:

1. A medicament for treating erectile dysfunction comprising a homeopathically potentised form of polyclonal, antibodies to endothelial nitric oxide synthase (NO synthase).

2. The medicament according to claim 1, wherein the polyclonal, antibodies are to the whole NO synthase enzyme.

3. A medicament for treating erectile dysfunction comprising homeopathically potentised form of polyclonal, antibodies are to a fragment of nitric oxide synthase (NO synthase), consisting of SEQ ID NO:1.

4. The medicament according to claim 1, wherein the polyclonal, antibodies are to a fragment of the NO synthase enzyme.

5. The medicament of claim 1, wherein said homeopathically potentised form comprises one or more homeopathic dilution.

6. The medicament of claim 3, wherein said homeopathically potentised form comprises one or more homeopathic dilution.

7. The medicament according to claim 5, wherein said one or more of the homeopathic dilutions comprises one or more centesimal homeopathic dilutions.

8. The medicament according to claim 6, wherein said one or more of the homeopathic dilutions comprises one or more centesimal homeopathic dilutions.

* * * * *

SEQUENCE LISTING

```
<160> NUMBER OF SEQ ID NOS: 1

<210> SEQ ID NO 1
<211> LENGTH: 21
<212> TYPE: PRT
<213> ORGANISM: Bos taurus

<400> SEQUENCE: 1

Arg His Leu Arg Gly Ala Val Pro Trp Ala Phe Asp Pro Pro Gly Pro
1               5                   10                  15

Asp Thr Pro Gly Pro
            20
```